United States Patent [19]

Parobek

[11] Patent Number: 4,959,848
[45] Date of Patent: Sep. 25, 1990

[54] APPARATUS FOR THE MEASUREMENT OF THE THICKNESS AND CONCENTRATION OF ELEMENTS IN THIN FILMS BY MEANS OF X-RAY ANALYSIS

[75] Inventor: Lubomir Parobek, San Jose, Calif.

[73] Assignee: AXIC Inc., Santa Clara, Calif.

[21] Appl. No.: 133,533

[22] Filed: Dec. 16, 1987

[51] Int. Cl.$^5$ ............................................. G01N 23/223
[52] U.S. Cl. ........................................ 378/46; 378/45; 378/48; 378/49; 378/50
[58] Field of Search ................... 378/44–46, 378/48–50, 142, 70, 71, 79, 80, 82, 83, 84, 85, 142

[56] References Cited

U.S. PATENT DOCUMENTS

| | | | |
|---|---|---|---|
| 2,132,174 | 10/1938 | Machlett | 378/142 |
| 2,504,706 | 4/1950 | Lempert et al. | 378/142 |
| 2,837,655 | 6/1958 | Lang | 378/83 |
| 2,837,656 | 6/1958 | Hendee et al. | 378/49 |
| 2,846,589 | 8/1958 | Pellissier et al. | 378/50 |
| 2,924,715 | 2/1960 | Hendee et al. | 378/49 |
| 3,196,272 | 7/1965 | Culbertson | 378/50 |
| 3,198,944 | 8/1965 | Furbee | 378/50 |
| 4,150,288 | 4/1979 | Inoue et al. | 378/50 |
| 4,162,528 | 7/1979 | Maldonado et al. | 378/50 |
| 4,236,072 | 11/1980 | Schinkel et al. | 378/83 |
| 4,365,156 | 12/1982 | Golouchenko et al. | 378/84 |
| 4,646,341 | 2/1987 | Finer et al. | 378/48 |
| 4,696,023 | 9/1987 | Kuusi | 378/46 |
| 4,764,945 | 8/1988 | Tadahiro | 378/50 |

FOREIGN PATENT DOCUMENTS

| | | | |
|---|---|---|---|
| 0163445 | 12/1980 | Japan | 378/71 |
| 0205842 | 11/1983 | Japan | 378/50 |
| 0223047 | 12/1983 | Japan | 378/44 |
| 0105547 | 6/1984 | Japan | 378/44 |
| 0202339 | 10/1985 | Japan | 378/44 |
| 0236052 | 11/1985 | Japan | 378/44 |
| 0003650 | 1/1987 | Japan | 378/44 |

Primary Examiner—Janice A. Howell
Assistant Examiner—John C. Freeman
Attorney, Agent, or Firm—Rosenblum, Parish & Bacigalupi

[57] ABSTRACT

A device which measures both the thickness of a thin film and the concentration of selected elements within the thin film. An X-ray source is utilized to irradiate the thin film sample and two detectors, an energy dispersive detector and a wavelength dispersive detector, provide the film thickness and element concentration measurements respectively.

10 Claims, 2 Drawing Sheets

APPARATUS FOR THE MEASUREMENT OF THE THICKNESS AND CONCENTRATION OF ELEMENTS IN THIN FILMS BY MEANS OF X-RAY ANALYSIS

BACKGROUND OF THE INVENTION

1. Field of the Invention

The present invention relates to X-ray devices utilized to measure thin films, and more particularly to an X-ray device which measures both the thickness and concentration of selected elements in a thin film.

2. Description of the Prior Art

The prior art includes patents which disclose devices that conduct the type of measurements performed by the present invention. However, the prior art does not apparently teach methods of combining the various measurements taken by the present invention in a single device.

SUMMARY OF THE INVENTION

It is an object of the present invention to provide an apparatus which simultaneously measures both thin film thickness and concentration of selected elements therein.

It is another object of the present invention to provide an apparatus which utilizes a single X-ray source to irradiate a sample and two X-ray detection systems, one of which measures thickness of the thin film, and the other which measures the concentration of selected elements in the thin film.

It is a further object of the present invention to provide an apparatus in which the X-ray source and the detectors are disposed in a helium atmosphere at approximately ambient pressure and wherein the test sample is disposed in the ambient air.

It is yet another object of the present invention to provide an apparatus in which the detector that measures thickness is disposed at a relatively acute angle with respect to the planar surface of the thin film to enhance accuracy of thickness measurement, and in which the detector that measures element concentration is disposed at a relatively large angle with respect to the surface of the thin film to enhance accuracy of the element concentration measurement of films where the measured concentration is not distributed uniformly through the thickness of the film.

It is yet a further object of the present invention to provide an apparatus which is relatively inexpensive to manufacture and simple to use.

It is still another object of the present invention to provide an apparatus which utilizes a built-in calibration sample to enhance accuracy, precision and consistency of the measurements provided by the apparatus.

The present invention includes a sealed spectrometer housing containing a helium atmosphere at slightly greater than ambient pressure. An X-ray source and two X-ray detection systems are disposed within the housing. A thin window is disposed on one face of the housing and the test sample is disposed in a holder immediately outside the window in ambient atmosphere. X-rays from the X-ray source are directed through the window to irradiate the sample. Fluorescing X-rays, emitted by atoms within the test sample, pass back through the window and are analyzed by the two spectrometer detection systems disposed within the housing.

A first X-ray detection system is utilized to determine the thickness of the thin film test sample by measuring the intensity of X-rays directed toward the detector through a collimator. A second X-ray detection system is utilized to quantitatively determine the concentration of selected elements within the thin film. The second X-ray detection system utilizes a crystal spectrometer which operates according to Bragg's Law and is tunable through rotation of the crystal and detector associated therewith. The test results from an unknown sample are compared to test results from a calibrated known sample to provide quantitative results.

It is an advantage of the present invention that it provides an apparatus which simultaneously measures both thin film thickness and concentration of selected elements therein.

It is another advantage of the present invention that it provides an apparatus which utilizes a single X-ray source to irradiate a sample and two X-ray detection systems, one of which measures thickness of the thin film, and the other which measures the concentration of selected elements in the thin film.

It is a further advantage of the present invention that it provides an apparatus in which the X-ray source and the detectors are disposed in a helium atmosphere at approximately ambient pressure and wherein the test sample is disposed in the ambient air.

It is yet another advantage of the present invention that it provides an apparatus in which the detector that measures thickness is disposed at a relatively acute angle with respect to the planar surface of the thin film to enhance accuracy of thickness measurement, and in which the detector that measures element concentration is disposed at a relatively large angle with respect to the surface of the thin film to enhance accuracy of the element concentration measurement of films where the measured concentration is not distributed uniformly through the thickness of the film.

It is yet a further advantage of the present invention that it provides an apparatus which is relatively inexpensive to manufacture and simple to use.

It is still another advantage of the present invention that it provides an apparatus which utilizes a built-in calibration sample to enhance accuracy, precision and consistency of the measurements provided by the apparatus.

The foregoing objects, features and advantages of the present invention will be apparent from the following detailed description of the preferred embodiment, which makes reference to the several figures of the drawing.

IN THE DRAWING

DESCRIPTION OF THE PREFERRED EMBODIMENT

Figure 1:
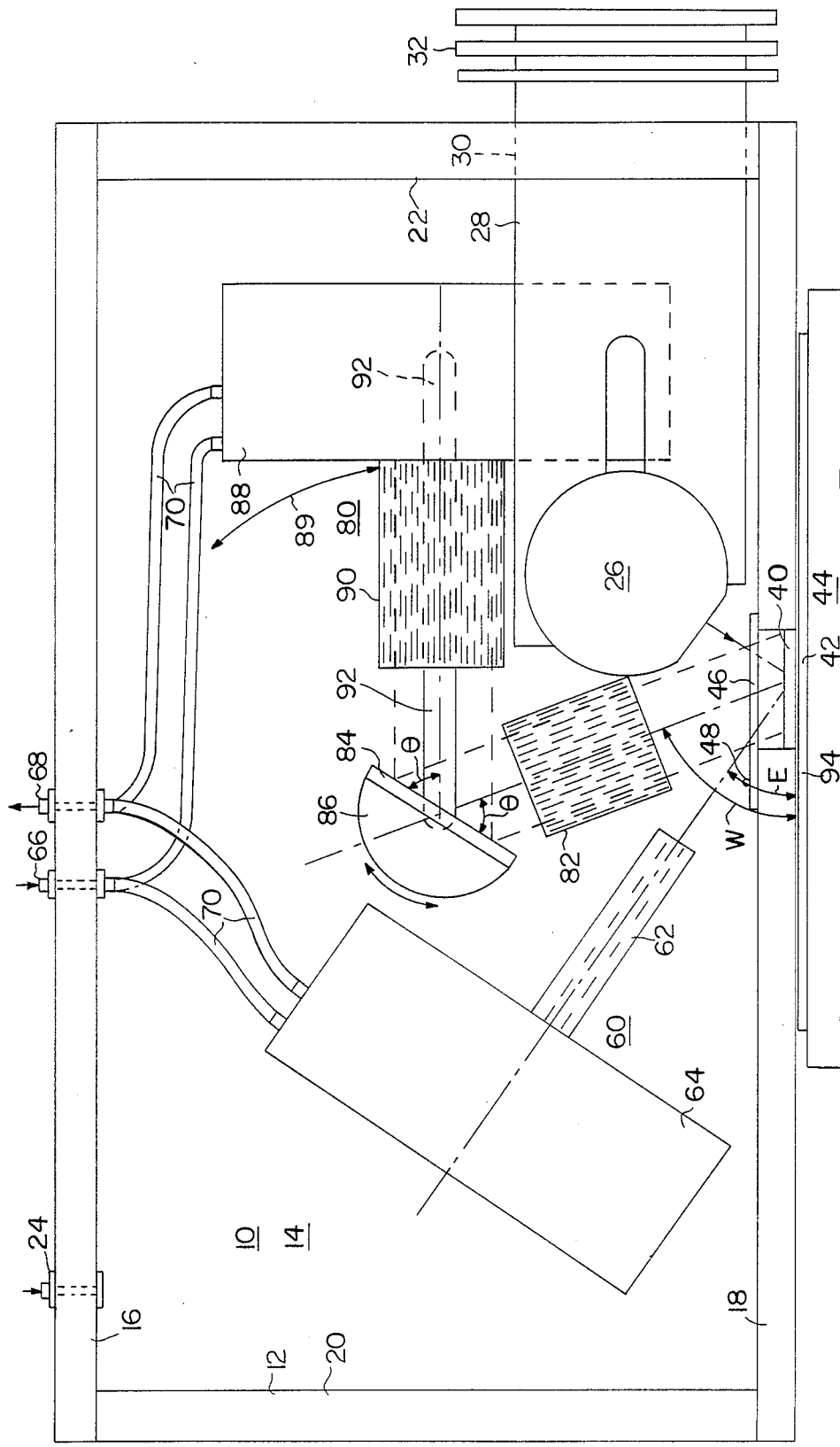
FIG. 1 is a schematic diagram of the present invention.

The present invention 10 includes a housing 12 within which the X-ray test systems reside. The housing 12 is formed as a box-like structure having a rear wall 14, front wall (shown removed in the schematic), top wall 16, bottom wall 18, side wall 20, and sidewall 22, all said walls being joined together to form an enclosed space surrounded by said housing 12. The walls are preferably composed of nickel-plated steel approximately one-half inch thick to provide shielding for the X-rays emitted within the housing during the utilization of the device. The X-ray emission and detection systems within the housing operate in a helium atmosphere at slightly greater than ambient pressure. Thus, a helium inlet aperture 24 is formed through a wall of the device, such as the top wall 16 to permit the establishment and maintenance of the helium atmosphere. Each of the seams between the walls of the device is sealed to prevent the rapid escape of the helium within the housing 12. Nevertheless, it has been found that the helium will slowly escape, wherefore the continual additional of helium gas from a source (not shown) through inlet 24 is necessary.

An X-ray source 26 is disposed within the housing to provide the X-rays that are utilized to irradiate a test sample during test procedures. In the preferred embodiment an air-cooled, Rhodium target X-ray tube utilizing a 40-watt power supply is utilized as the X-ray source 26. As depicted in FIG. 1, a thermally-conductive copper rod 28 is utilized to make physical contact with the hot X-ray source 26 and conduct heat therefrom, through a hole 30 formed in a wall 22 of the housing 12, to a heat-radiating finned member 32 disposed in the ambient air atmosphere outside of the housing 12.

A thin window 40 is disposed in one face, such as bottom face 18, of the housing 12. The window 40 is formed of a material and thickness sufficient to hold the helium within the housing 12 and present minimal interference with X-rays passing therethrough. A thin window 40 formed from polyester having a thickness of approximately 4 microns has been found to be suitable for the preferred embodiment described herein. A test sample 42, such as an integrated circuit chip wafer having a thin film formed thereon resides upon a sample holder 44 that is disposed on the atmospheric side of the window 40. The X-ray source 26 is disposed within the housing 12 in close proximity to the window 40, such that the X-rays emitted from the source 26 will travel a minimal distance before passing through the window 40 to encounter the thin film test sample 42. The utilization of a helium atmosphere within the housing 12 having a pressure only slightly above atmospheric pressure thus allows the use of a relatively large yet thin detector window 40.

In the preferred embodiment a window shutter 46 is slideably engaged to the housing 12, such as by utilization of a pivot pin 48, to cover the window 40 between actual tests while the apparatus is being operated. During actual testing of a sample the shutter 46 is removed from the window 40. The utilization of the shutter, which blocks X-rays from passage through the window 40, permits the X-ray source 26 to operate continuously both during and between actual tests, thus promoting consistency of X-ray flux throughout a series of tests and enhancing the accuracy of the apparatus.

Two X-ray detector systems 60 and 80 are disposed within the housing 12. The first detector system 60 includes a collimator 62 positioned to accept X-rays emitted from the sample 42 and direct them into an X-ray detector 64. In the preferred embodiment, the collimator 62 is formed as an aluminum tube having a bore of approximately 1.5 millimeters. The central axis of the bore of the collimator 62 is aligned at the relatively shallow angle E with respect to the surface plane of the thin film test sample 42. In the preferred embodiment, angle E is approximately 30 degrees. It is therefore to be appreciated that the detector system 60 functions as an energy dispersive spectrometer (EDS) which detects X-rays of all wavelengths which pass through collimator 62. Measurements taken by the EDS detector system 60 are thus related to the thickness of the thin film of the test sample.

In the preferred embodiment the X-ray detector 64 comprises a flow proportional detector utilizing an argon-methane gas atmosphere. An argon-methane gas inlet 66 and outlet 68 are disposed through a wall of the housing 12 and are connected to the detector 64 by suitable tubing 70. Such detectors are well known to the ordinarily skilled person and the invention is not to be limited to such detectors; other suitable X-ray detectors may be substituted therefor.

The second detector system 80 disposed within the housing 12 comprises a crystal spectrometer which is utilized as a wavelength dispersive spectrometer (WDS). The detector system 80 includes a first parallel plate collimator 82 having a central axis which is disposed at a relatively large angle W of approximately 70 degrees with respect to the surface plane of the thin film test sample 42. The detector system 80 further includes a crystal 84 that is aligned to receive X-rays passing through collimator 82. The crystal 84 is composed of a material having a crystal lattice which acts as an X-ray diffraction crystal. The crystal 84 is demountably engaged to a rotateable holder 86, such that the angle $\theta$ between the impinging X-rays from the collimator 82 and the surface plane of the crystal 84 is adjustable by the user of the apparatus by rotation of the holder 86 through $\Delta\theta$.

A second X-ray detector 88 is disposed within the housing 12 to receive X-rays diffracted from crystal 84 at an adjustable angle $\theta$ to the surface plane of the crystal 84. An X-ray collimator 90 is fixedly engaged to the detector 88 and oriented relative to the crystal 84 to collimate X-rays emerging from the crystal 84 at angle $\theta$. The detector 88 and its fixedly-engaged collimator 90 are mounted on a rotateable arm 92 having an axis of rotation that is concentric with the axis of rotation of the crystal holder 86. The arm 92 of the detector 88 is mounted on a two to one ratio gear (not shown) such that the rotation of the crystal holder 86 through an angle $\Delta\theta$ will result in the rotation of the detector 88 along arc 89 through an angle $2\Delta\theta$. Thus the collimator 90 will retain its alignment with the crystal 84 and the new angle of incidence $\theta$ plus $\Delta\theta$ will equal the new angle of diffraction $\theta$ plus $\Delta\theta$. Those skilled in the art will therefore understand through the application of Bragg's Law that by rotating the crystal 84 to different known angles that the X-rays of particular wavelengths will be diffracted from the crystal 84 into the detector 88, whereby a quantitative determination of particular elements in the thin film can be determined.

A calibrated sample 94 (shown in phantom in FIG. 1) is demonstrably engaged to the sample holder 44 proximate the test sample 42. The sample holder 44 is disposed to move relative to the window 40 to permit exposure of the calibrated sample 94 to the X-ray source. The calibrated sample 94 is utilized to provide quantitative results regarding the thickness of the thin film and the concentration of a selected element within the film. Results from the calibrated sample, having a known thin film thickness within the range of the test sample, and a known concentration of the selected element, within the range of the test sample, are compared with the test sample results to provide quantitative information. The ease of access of the operator to the calibrated sample greatly facilitates the frequent calibration of the device, whereby the accuracy, precision and consistency of results is enhanced. A basic understanding of the operation of the device follows.

When radiation from an X-ray tube or radioactive source is allowed to excite the atoms of a sample, inner shell (K, L and M) electrons are removed in the ionization process. When electrons from the outer shells fill the inner shell vacancies, characteristic X-rays, unique to each element and shell are generated. Detection of these characteristic X-rays allows qualitative and quantitative analysis of the elements present in the sample.

In the present invention, radiation from a Rhodium targeted X-ray tube 26 is sufficient to excite (fluoresce) atoms of Si, P, W, Cu and others in a test sample 42 wafer normally associated with semiconductor thin film applications. The X-rays are sufficiently energetic to pass through many microns of most films and enter the substrate (i.e. silicon, sapphire, gallium arsenide, and others). The resultant characteristic fluoresced X-rays are generated from the coating and the substrate. Utilizing the two different X-ray detection systems 60 and 80, which conduct energy dispersive spectrometry (EDS) and wavelength dispersive spectrometry (WDS) respectively, both film thickness and Wt. % of the element being analyzed are simultaneously determined.

The element to be analyzed is accurately selected by varying the WDS crystal spectrometer angle $\theta$ prior to analysis. Elemental qualitative analysis is determined according to the Bragg equation $\lambda = 2d \sin \theta$ where:

$\lambda$ is the Wavelength of the characteristic X-ray d is the spacing between the atoms in the single crystal, and $\theta$ is the angle between the crystal surface and the diffracted X-rays Quantitative analysis is obtained by comparing the X-ray signal from the unknown to a known reference.

Figure 2:
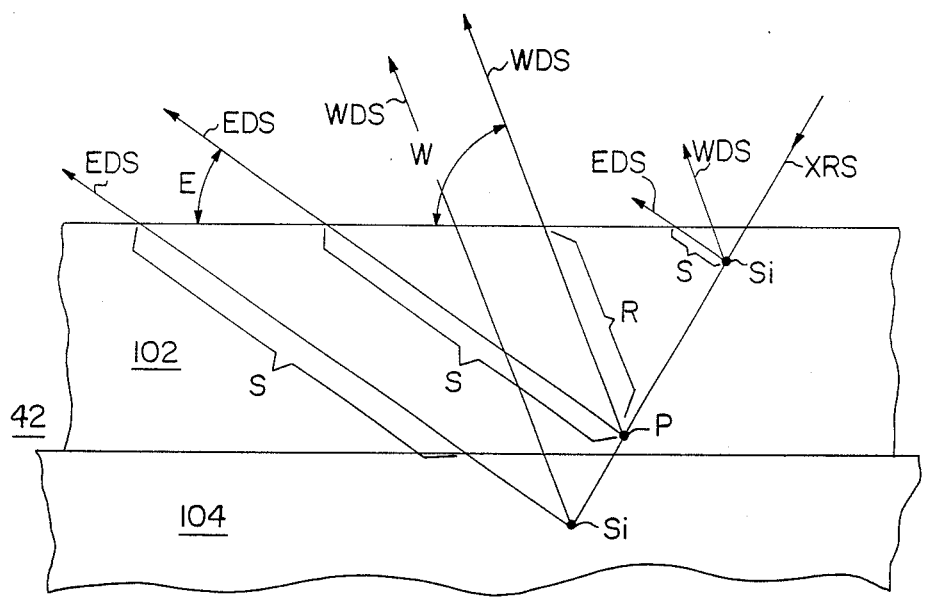
FIG. 2 depicts the angular relationships between the X-ray impingement and emission-detection angles relative to a thin film test sample.

FIG. 2 depicts a greatly enlarged view of the interaction of an X-ray with a thin film. As depicted therein, a test sample 42 includes a thin film 102 disposed upon a substrate 104. An X-ray, represented by a vector from the X-ray source (XRS) excites a phosphorus atom P and silicon atoms Si disposed within the thin film 102 an within the substrate 104. Emitted characteristic X-rays from the phosphorus and silicon atoms travel to the two detectors represented by vectors directed towards the energy dispersive system (EDS) 60 and the wavelength dispersive system (WDS) 80. As depicted in FIG. 2, the EDS vector is disposed at a relatively shallow angle E with respect to the planar surface of the film 102, whereupon X-rays emitted from the phosphorus and silicon atoms travel a relatively long distance S through the film 102 before reaching the surface thereof. Because the X-rays emitted by the atoms in the sample traverse a relatively long distance S through the thin film 102, they are attenuated to a greater degree than X-rays that might travel a shorter distance if angle E were larger. The greater attenuation of the X-rays by the film corresponds to greater accuracy in the thickness measurement of the film by the detector system 60 that is disposed along the EDS vector.

As is seen in FIG. 2, X-rays emitted by the phosphorus atom along the WDS vector emerge at a relatively large angle W with respect to the planar surface of the thin film. Due to the relatively large angle W, X-rays emitted along vector WDS travel a relatively short distance R through the thin film 102 and are therefore attenuated to a minimal degree. The minimal attenuation leads to a greater X-ray intensity along vector WDS which results in a stronger signal and greater accuracy of the WDS detector system 80.

While the invention has been particularly shown and described with reference to a certain preferred embodiment, it will be understood by those skilled in the art that various alterations and modifications in form and detail may be made therein. Accordingly, it is intended that the following claims cover all such alterations and modifications as fall within the true spirit and scope of the invention.

What I claim is:

1. An apparatus for the measurement of the thickness of a thin film disposed upon a substrate and the quantitative determination of certain elements within said thin film comprising:

a housing formed from at least one wall defining an enclosed space;

a window disposed within a wall of said housing and functioning to permit X-rays to pass therethrough;

an X-ray source within said housing and oriented therewithin to cause x-rays to be directed through said window;

a test sample holder disposed proximate said window and outside of said housing and functioning to hold a test sample outside of said housing in close proximity to said window such that said test sample will be irradiated by said X-rays;

a first X-ray detection system being fixedly engaged within said housing and operable to detect X-rays emitted from atoms within said test sample through said window, said first X-ray detection system providing a measurement through the detection of a broad energy spectrum of X-rays from all emitting elements of said test sample;

a second X-ray detection system being movably engaged within said housing and operable to detect X-rays emitted from said atoms within said test sample and passing through said window, said second X-ray system being turnable to detect X-rays of a selected narrow wavelength band for measurement;

said measurement first said first X-ray detection system being utilized to determine the thickness of said thin film, and said measurement from said second X-ray detection system being utilized to provide a quantitative measurement of the content of particular elements within said thin film.

2. An apparatus as described in claim 1, further including an atmosphere of helium gas being disposed within said housing at a pressure slightly greater than atmospheric pressure.

3. An apparatus as described in claim 1 wherein said first X-ray detection system includes a first X-ray detector comprising an energy dispersive spectrometer (EDS) and a collimator that is disposed between said window and said first detector.

4. The apparatus as described in claim 1 wherein said second X-ray detection system includes a wavelength dispersive spectrometer (WDS) which detects X-rays of a selected wavelength according to Bragg's Law.

5. The apparatus as described in claim 4 wherein said wavelength dispersive spectrometer includes a crystal mountably engaged to a rotatable holder and wherein a first collimator is disposed between said window and said crystal;

said second X-ray detection system including a second X-ray detector having a second collimator fixedly engaged thereto and oriented to pass X-rays diffracted from said crystal therethrough to said second detector.

6. The apparatus as described in claim 5 wherein said second X-ray detector and said second collimator are engaged to a rotatable arm, said, rotatable arm being operable to cause said second X-ray detector to sweep through an arc of $2\Delta\theta$ whenever said crystal holder is rotated through an angle of $\Delta\theta$.

7. The apparatus as described in claim 1 wherein said first detector is mounted within said housing at a relatively shallow angle with respect to the planar surface of said test sample, and wherein said second X-ray detection system is disposed within said housing at relatively large tunable angles with respect to the planar surface of said test sample.

8. The apparatus as described in claim 1 wherein a means is provided to air cool said X-ray source.

9. The apparatus as described in claim 8 wherein said X-ray source cooling means includes a heat-conducting member being engaged to said X-ray source at one end thereof and passing through said housing and being joined to a finned heat-radiating member at the other end thereof.

10. The apparatus as described in claim 1 wherein a calibrated sample is mountably engaged to said test sample holder;

said test sample holder being operable to place said calibrated sample in position proximate said window for irradiation by said X-rays.

* * * * *